United States Patent
Gui et al.

(10) Patent No.: US 8,592,548 B2
(45) Date of Patent: Nov. 26, 2013

(54) METHOD TO PREPARE BIS(HALOIMIDES)

(75) Inventors: John Yupeng Gui, Niskayuna, NY (US); Norman Enoch Johnson, Mt. Vernon, IN (US); Thomas Link Guggenheim, Mt. Vernon, IN (US); David Winfield Woodruff, Saratoga Springs, NY (US); James Manio Silva, Clifton Park, NY (US); Farid Fouad Khouri, Clifton Park, NY (US)

(73) Assignee: Sabic Innovative Plastics IP B.V. (NL)

( * ) Notice: Subject to any disclaimer, the term of this patent is extended or adjusted under 35 U.S.C. 154(b) by 21 days.

(21) Appl. No.: 11/022,907

(22) Filed: Dec. 22, 2004

(65) Prior Publication Data

US 2006/0135741 A1   Jun. 22, 2006

(51) Int. Cl.
*C08G 8/02* (2006.01)

(52) U.S. Cl.
USPC ............. 528/125; 528/26; 528/126; 528/128; 528/170; 528/171; 528/353; 528/425

(58) Field of Classification Search
USPC ........... 528/125, 26, 126, 128, 170, 171, 353, 528/425
See application file for complete search history.

(56) References Cited

U.S. PATENT DOCUMENTS

| | | | |
|---|---|---|---|
| 3,748,340 A | 7/1973 | Hayes | |
| 3,787,364 A | 1/1974 | Wirth et al. | |
| 3,838,108 A * | 9/1974 | Hergenrother et al. | 528/73 |
| 3,875,116 A | 4/1975 | Heath et al. | |
| 5,182,392 A | 1/1993 | Tanisake et al. | |
| 5,229,482 A | 7/1993 | Brunelle | |
| 5,817,425 A | 10/1998 | Morishige et al. | |
| 5,830,974 A | 11/1998 | Schmidhauser et al. | |
| 6,096,134 A | 8/2000 | Zhao et al. | |
| 6,235,866 B1 * | 5/2001 | Khouri et al. | 528/125 |
| 6,248,879 B1 | 6/2001 | Anderson et al. | |
| 7,981,996 B2 | 7/2011 | Khouri et al. | |
| 2006/0135741 A1 | 6/2006 | Gui et al. | |
| 2006/0224024 A1 | 10/2006 | Silva et al. | |

FOREIGN PATENT DOCUMENTS

| | | |
|---|---|---|
| EP | 0 892 003 | 1/1999 |
| WO | WO 01/25196 | 4/2001 |
| WO | WO 2005/023903 | 3/2005 |

OTHER PUBLICATIONS

International Search Report dated Aug. 4, 2006.
International Search Report; International Application No. PCT/US2005/045590; International Filing Date: Dec. 15, 2005; 3 pages.
Written Opinion of the International Searching Authority; International Application No. PCT/US2005/045590; International Filing Date: Dec. 15, 2005; Date of Mailing: Aug. 4, 2006; 5 Pages.

* cited by examiner

*Primary Examiner* — Gregory Listoyb
(74) *Attorney, Agent, or Firm* — Cantor Colburn LLP; Diderico van Eyl

(57) ABSTRACT

Bis(halophthalimides) are prepared in mixture in an organic liquid such as ortho-dichlorobenzene or anisole, by a reaction at a temperature of at least 150° C. between at least one diamine compound and at least one halophthalic anhydride in the presence of imidization catalyst. The reaction mixture is maintained at about 15% by weight solids content and rich in the halophthalic anhydride by constantly monitoring the reaction mixture using analytical methods such as high performance liquid chromatography. The product mixture may be directly employed in the direct preparation of polyetherimides, and similar slurries may be employed to prepare other polyether polymers.

31 Claims, No Drawings

METHOD TO PREPARE BIS(HALOIMIDES)

BACKGROUND OF THE INVENTION

This invention relates to an improved method for the preparation of bis(halophthalimides), monomers useful for the preparation of polyetherimides.

Various types of polyethers, such as polyetherimides, polyethersulfones, polyetherketones, and polyethertherketones, have become important as engineering resins by reason of their excellent properties. These polymers are typically prepared by the reaction of dihydroxyaromatic compounds, such as bisphenol A disodium salt, with dihaloaromatic compounds. For example, polyetherimides are conveniently prepared by the reaction of salts of dihydroxyaromatic compounds with bis(halophthalimides).

U.S. Pat. Nos. 5,229,482 and 5,830,974, disclose the preparation of aromatic polyethers in relatively non-polar solvents, using a phase transfer catalyst which is substantially stable under the polymerization conditions. Solvents disclosed in U.S. Pat. No. 5,229,482 include o-dichlorobenzene, dichlorotoluene, 1,2,4-trichlorobenzene and diphenyl sulfone. U.S. Pat. No. 5,830,974 discloses the use of solvents such as anisole, diphenylether, and phenetole. Solvents of the same type may be used for the preparation of bis(halophthalimide) intermediates for polyetherimides.

In each of U.S. Pat. Nos. 5,229,482 and 5,830,974 the bis(halophthalimide) is introduced into the polymerization reaction as a substantially pure, isolated compound. This process step is often difficult, since solid bis(halophthalimides) are typically of very low density and fluffy, making weighing and handling burdensome. U.S. Pat. No. 6,235,866 teaches a method of slurry preparation of bis(halophthalimides) by the reaction between diamine compounds and halophthalic anhydride, in equimolar proportions and use of that slurry as such to prepare polyether polymers. But in the disclosed process, considerable caking of the product bis(halophthalimides) occurs, rendering the product difficult to isolate as a pure slurry, resulting in unacceptable levels of residual starting material in the polymer. Also, the presence of water in the resulting product has a deleterious effect on the molecular weight of the polymer. If proper stoichiometric balance between the diamine and the halophthalic anhydride is not maintained, several undesirable by-products remain in the slurry which limit the molecular weight of the polymer, and/or result in polymers with amine end groups Thus there is a need in the art to develop a facile process for the preparation of bis(halophthalimides) having suitable characteristics for conversion to polyetherimide polymers without isolation which overcomes the shortcomings of current synthetic methods.

BRIEF SUMMARY OF THE INVENTION

The present invention provides a method for preparing a bis(halophthalimide), said method comprising:

(A) preparing a mixture comprising at least one halophthalic anhydride and at least one solvent, (B) adding to the mixture formed in step (A) at least one diamine, to form a reaction mixture, said reaction mixture being characterized by "an initial molar ratio of halophthalic anhydride to diamine";

(C) heating the reaction mixture formed in step (B) to a temperature of at least 100° C., optionally in the presence of an imidization catalyst;

(D) analyzing the reaction mixture formed by the combination of steps (A)-(C) to determine the initial molar ratio of halophthalic anhydride to diamine; and (E) performing one step selected from the group consisting of:

(i) adding anhydride or diamine to the mixture formed by the combination of steps (A)-(C) to achieve a "corrected molar ratio" of halophthalic anhydride to diamine, said corrected molar ratio being in a range between about 2.01 and about 2.3, and heating to a temperature of at least 100° C., optionally in the presence of an imidization catalyst, to obtain a bis(halophthalimide) product mixture that is substantially free of water; and (ii) heating to a temperature of at least 100° C., optionally in the presence of an imidization catalyst, the reaction mixture formed by the combination of steps (A)-(C) to obtain a bis(halophthalimide) product mixture that is substantially free of water.

DETAILED DESCRIPTION OF THE INVENTION

The present invention may be understood more readily by reference to the following detailed description of preferred embodiments of the invention and the examples included therein. In the following specification and the claims which follow, reference will be made to a number of terms which shall be defined to have the following meanings:

The singular forms "a", "an" and "the" include plural referents unless the context clearly dictates otherwise.

"Optional" or "optionally" means that the subsequently described event or circumstance may or may not occur, and that the description includes instances where the event occurs and instances where it does not.

As used herein the term "integer" means a whole number which includes zero. For example, the expression "n is an integer from 0 to 4" means "n" may be any whole number from 0 to 4 including 0 and 4. Similarly, the expression "an integer ranging from 1 to 4 inclusive" means an integer in a range from 1 to 4, said range including the integer 1 and the integer 4.

As used herein the term "aliphatic radical" refers to an organic radical having a valence of at least one consisting of a linear or branched array of atoms which is not cyclic. Aliphatic radicals are defined to comprise at least one carbon atom. The array of atoms comprising the aliphatic radical may include heteroatoms such as nitrogen, sulfur, silicon, selenium and oxygen or may be composed exclusively of carbon and hydrogen. For convenience, the term "aliphatic radical" is defined herein to encompass, as part of the "linear or branched array of atoms which is not cyclic" a wide range of functional groups such as alkyl groups, alkenyl groups, alkynyl groups, haloalkyl groups, conjugated dienyl groups, alcohol groups, ether groups, aldehyde groups, ketone groups, carboxylic acid groups, acyl groups (for example carboxylic acid derivatives such as esters and amides), amine groups, nitro groups, and the like. For example, the 4-methylpent-1-yl radical is a $C_6$ aliphatic radical comprising a methyl group, the methyl group being a functional group which is an alkyl group. Similarly, the 4-nitrobut-1-yl group is a $C_4$ aliphatic radical comprising a nitro group, the nitro group being a functional group. An aliphatic radical may be a haloalkyl group which comprises one or more halogen atoms which may be the same or different. Halogen atoms include, for example; fluorine, chlorine, bromine, and iodine. Aliphatic radicals comprising one or more halogen atoms include the alkyl halides trifluoromethyl, bromodifluoromethyl, chlorodifluoromethyl, hexafluoroisopropylidene, chloromethyl, difluorovinylidene, trichloromethyl, bromodichloromethyl, bromoethyl, 2-bromotrimethylene (e.g., —CH$_2$CHBrCH$_2$—), and the like. Further examples of aliphatic radicals include allyl, aminocarbonyl (i.e. —CONH$_2$), carbonyl, 2,2-dicyanoisopropylidene (i.e., —CH$_2$C(CN)$_2$CH$_2$—), methyl (i.e., —CH$_3$), methylene (i.e., —CH$_2$—), ethyl, ethylene, formyl (i.e., —CHO), hexyl, hexamethylene, hydroxymethyl (i.e., —CH$_2$OH), mercaptomethyl (i.e., —CH$_2$SH), methylthio (i.e., —SCH$_3$), methylthiomethyl (i.e., —CH$_2$SCH$_3$), methoxy, methoxycarbonyl (i.e., CH$_3$OCO—), nitromethyl (i.e., —CH$_2$NO$_2$), thiocarbonyl, trimethylsilyl (i.e., (CH$_3$)$_3$Si—), t-butyldimethylsilyl, 3-trimethyoxysilypropyl (i.e., (CH$_3$O)$_3$SiCH$_2$CHCH$_2$CH—), vinyl, vinylidene, and the like. By way of further example, a C$_1$-C$_{10}$ aliphatic radical contains at least one but no more than 10 carbon atoms. A methyl group (i.e., CH$_3$—) is an example of a C$_1$ aliphatic radical. A decyl group (i.e., CH$_2$(CH$_2$)$_9$—) is an example of a C$_{10}$ aliphatic radical.

As used herein, the term "aromatic radical" refers to an array of atoms having a valence of at least one comprising at least one aromatic group. The array of atoms having a valence of at least one comprising at least one aromatic group may include heteroatoms such as nitrogen, sulfur, selenium, silicon and oxygen, or may be composed exclusively of carbon and hydrogen. As used herein, the term "aromatic radical" includes but is not limited to phenyl, pyridyl, furanyl, thienyl, naphthyl, phenylene, and biphenyl radicals. As noted, the aromatic radical contains at least one aromatic group. The aromatic group is invariably a cyclic structure having 4n+2 "delocalized" electrons where "n" is an integer equal to 1 or greater, as illustrated by phenyl groups (n=1), thienyl groups (n=1), furanyl groups (n=1), naphthyl groups (n=2), azulenyl groups (n=2), anthraceneyl groups (n=3) and the like. The aromatic radical may also include nonaromatic components. For example, a benzyl group is an aromatic radical which comprises a phenyl ring (the aromatic group) and a methylene group (the nonaromatic component). Similarly a tetrahydronaphthyl radical is an aromatic radical comprising an aromatic group (C$_6$H$_3$) fused to a nonaromatic component —(CH$_2$)$_4$—. For convenience, the term "aromatic radical" is defined herein to encompass a wide range of functional groups such as alkyl groups, alkenyl groups, alkynyl groups, haloalkyl groups, haloaromatic groups, conjugated dienyl groups, alcohol groups, ether groups, aldehydes groups, ketone groups, carboxylic acid groups, acyl groups (for example carboxylic acid derivatives such as esters and amides), amine groups, nitro groups, and the like. For example, the 4-methylphenyl radical is a C$_7$ aromatic radical comprising a methyl group, the methyl group being a functional group which is an alkyl group. Similarly, the 2-nitrophenyl group is a C$_6$ aromatic radical comprising a nitro group, the nitro group being a functional group. Aromatic radicals include halogenated aromatic radicals such as 4-trifluoromethylphenyl, hexafluoroisopropylidenebis(4-phen-1-yloxy) (i.e., —OPhC(CF$_3$)$_2$PhO—), 4-chloromethylphen-1-yl, 3-trifluorovinyl-2-thienyl, 3-trichloromethylphen-1-yl (i.e., 3-CCl$_3$Ph-), 4-(3-bromoprop-1-yl)phen-1-yl (i.e., 4-BrCH$_2$CH$_2$CH$_2$Ph-), and the like. Further examples of aromatic radicals include 4-allyloxyphen-1-oxy, 4-aminophen-1-yl (i.e., 4-H$_2$NPh-), 3-aminocarbonylphen-1-yl (i.e., NH$_2$COPh-), 4-benzoylphen-1-yl, dicyanomethylidenebis(4-phen-1-yloxy) (i.e., —OPhC(CN)$_2$PhO—), 3-methylphen-1-yl, methylenebis(4-phen-1-yloxy) (i.e., —OPhCH$_2$PhO—), 2-ethylphen-1-yl, phenylethenyl, 3-formyl-2-thienyl, 2-hexyl-5-furanyl, hexamethylene-1,6-bis(4-phen-1-yloxy) (i.e., —OPh(CH$_2$)$_6$PhO—), 4-hydroxymethylphen-1-yl (i.e., 4-HOCH$_2$Ph-), 4-mercaptomethylphen-1-yl (i.e., 4-HSCH$_2$Ph-), 4-methylthiophen-1-yl (i.e., 4-CH$_3$SPh-), 3-methoxyphen-1-yl, 2-methoxycarbonylphen-1-yloxy (e.g., methyl salicyl), 2-nitromethylphen-1-yl (i.e., 2-NO$_2$CH$_2$Ph), 3-trimethylsilylphen-1-yl, 4-t-butyldimethylsilylphenl-1-yl, 4-vinylphen-1-yl, vinylidenebis (phenyl), and the like. The term "a C$_3$-C$_{10}$ aromatic radical" includes aromatic radicals containing at least three but no more than 10 carbon atoms. The aromatic radical 1-imidazolyl (C$_3$H$_2$N$_2$—) represents a C$_3$ aromatic radical. The benzyl radical (C$_7$H$_8$—) represents a C$_7$ aromatic radical.

As used herein the term "cycloaliphatic radical" refers to a radical having a valence of at least one, and comprising an array of atoms which is cyclic but which is not aromatic. As defined herein a "cycloaliphatic radical" does not contain an aromatic group. A "cycloaliphatic radical" may comprise one or more noncyclic components. For example, a cyclohexylmethyl group (C$_6$H$_{11}$CH$_2$—) is an cycloaliphatic radical which comprises a cyclohexyl ring (the array of atoms which is cyclic but which is not aromatic) and a methylene group (the noncyclic component). The cycloaliphatic radical may include heteroatoms such as nitrogen, sulfur, selenium, silicon and oxygen, or may be composed exclusively of carbon and hydrogen. For convenience, the term "cycloaliphatic radical" is defined herein to encompass a wide range of functional groups such as alkyl groups, alkenyl groups, alkynyl groups, haloalkyl groups, conjugated dienyl groups, alcohol groups, ether groups, aldehyde groups, ketone groups, carboxylic acid groups, acyl groups (for example carboxylic acid derivatives such as esters and amides), amine groups, nitro groups, and the like. For example, the 4-methylcyclopent-1-yl radical is a C$_6$ cycloaliphatic radical comprising a methyl group, the methyl group being a functional group which is an alkyl group. Similarly, the 2-nitrocyclobut-1-yl radical is a C$_4$ cycloaliphatic radical comprising a nitro group, the nitro group being a functional group. A cycloaliphatic radical may comprise one or more halogen atoms which may be the same or different. Halogen atoms include, for example; fluorine, chlorine, bromine, and iodine. Cycloaliphatic radicals comprising one or more halogen atoms include 2-trifluoromethylcyclohex-1-yl, 4-bromodifluoromethylcyclooct-1-yl, 2-chlorodifluoromethylcyclohex-1-yl, hexafluoroisopropylidene-2,2-bis(cyclohex-4-yl) (i.e., —C$_6$H$_{10}$C(CF$_3$)$_2$C$_6$H$_{10}$—), 2-chloromethylcyclohex-1-yl, 3-difluoromethylenecyclohex-1-yl, 4-trichloromethylcyclohex-1-yloxy, 4-bromodichloromethylcyclohex-1-ylthio, 2-bromoethylcyclopent-1-yl, 2-bromopropylcyclohex-1-yloxy (e.g., CH$_3$CHBrCH$_2$C$_6$H$_{10}$—), and the like. Further examples of cycloaliphatic radicals include 4-allyloxycyclohex-1-yl, 4-aminocyclohex-1-yl (i.e., H$_2$C$_6$H$_{10}$—), 4-aminocarbonylcyclopent-1-yl (i.e., NH$_2$COC$_5$H$_8$—), 4-acetyloxycyclohex-1-yl, 2,2-dicyanoisopropylidenebis(cyclohex-4-yloxy) (i.e., —OC$_6$H$_1$C(CN)$_2$C$_6$H$_{10}$O—), 3-methylcyclohex-1-yl, methylenebis(cyclohex-4-yloxy) (i.e., —OC$_6$H$_{10}$CH$_2$C$_6$H$_{10}$O—), 1-ethylcyclobut-1-yl, cyclopropylethenyl, 3-formyl-2-terahydrofuranyl, 2-hexyl-5-tetrahydrofuranyl, hexamethylene-1,6-bis(cyclohex-4-yloxy) (i.e., —OC$_6$H$_{10}$(CH$_2$)$_6$C$_6$H$_{10}$O—), 4-hydroxymethylcyclohex-1-yl (i.e., 4-HOCH$_2$C$_6$H$_{10}$—), 4-mercaptomethylcyclohex-1-yl (i.e., 4-HSCH$_2$C$_6$H$_{10}$—), 4-methylthiocyclohex-1-yl (i.e., 4-CH$_3$SC$_6$H$_{10}$O—), 4-methoxycyclohex-1-yl, 2-methoxycarbonylcyclohex-1-yloxy(2-CH$_3$OCOC$_6$H$_{10}$O—), 4-nitromethylcyclohex-1-yl (i.e., NO$_2$CH$_2$C$_6$H$_{10}$—), 3-trimethylsilylcyclohex-1-yl, 2-t-butyldimethylsilylcyclopent-1-yl, 4-trimethoxysilylethylcyclohex-1-yl (e.g., (CH$_3$O)SiCH$_2$CH$_2$C$_6$H$_{10}$—), 4-vinylcyclohexen-1-yl, vinylidenebis (cyclohexyl), and the like. The term "a C$_3$-C$_{10}$ cycloaliphatic radical" includes cycloaliphatic radicals containing at least three but no more than 10 carbon atoms. The cycloaliphatic radical 2-tetrahydrofuranyl ($C_4H_7O$—) represents a $C_4$ cycloaliphatic radical. The cyclohexylmethyl radical ($C_6H_{11}CH_2$—) represents a $C_7$ cycloaliphatic radical.

As noted the present invention relates to a method for the efficient preparation of bis(halophthalimides). In one embodiment the present invention relates to a method for the preparation of bis(halophthalimides) having structure I

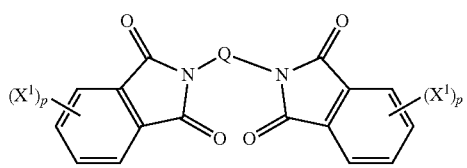

wherein $X^1$ is independently in each instance, a fluorine, chlorine, bromine or iodine group; and Q is a $C_2$-$C_{20}$ divalent aliphatic radical, a $C_2$-$C_{40}$ divalent aromatic radical, or a $C_4$-$C_{20}$ divalent cycloaliphatic radical; p is independently at each occurrence an integer in a range from 1 to 4 inclusive.

Bis(halophthalimides) having structure I are illustrated by 1,3-bis[N-(4-chlorophthalimido)]benzene (hereinafter sometimes "ClPAMI"). It should be noted that bis(halophthalimides) prepared from a mixture of 3-chlorophthalic anhydride and 4-chlorophthalic anhydride are also at times referred to as "ClPAMI".

There is no particular limitation on the diamine component. Any diamine compound may be employed and used according to the method of this invention. Typically, the diamine compound comprises at least one compound having structure II:

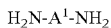

wherein $A^1$ is a $C_2$-$C_{20}$ divalent aliphatic radical, a $C_2$-$C_{40}$ divalent aromatic radical, or a $C_4$-$C_{20}$ divalent cycloaliphatic radical. Suitable aliphatic diamine compounds represented by structure II ($A^1$ is a $C_2$-$C_{20}$ divalent aliphatic radical) include ethylenediamine, 1,3-diaminopropane, 1,4-diaminobutane, 1,6-diaminohexane, and 1,10-diaminodecane. Suitable aromatic diamine compounds represented by structure II ($A^1$ is a $C_2$-$C_{40}$ divalent aromatic radical) include 1,4-diaminonaphthalene, 2,6-diaminonaphthalene, 4,4'-diaminobiphenyl, and the like. Suitable cycloaliphatic diamine compounds represented by structure II ($A^1$ is a $C_4$-$C_{20}$ divalent cycloaliphatic radical) include trans-1,2-diaminocyclopentane, trans-1,4-(bis aminomethyl)cyclohexane, and the like.

In one embodiment, the diamine compound is selected from the group consisting of oxydianiline, bis(4-aminophenyl)sulfone, meta-phenylenediamine, para-phenylenediamine, and mixtures thereof.

In a preferred embodiment of the invention, the diamine compound is selected from the group represented by structures III and IV

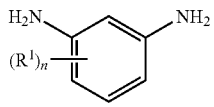

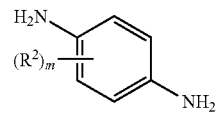

wherein $R^1$ and $R^2$ are independently at each occurrence a halogen atom, a nitro group, a cyano group, a $C_2$-$C_{20}$ aliphatic radical, a $C_2$-$C_{40}$ aromatic radical, or a $C_4$-$C_{20}$ divalent aliphatic radical; and "n" and "m" are independently integers ranging from about 0 to about 4. Examples of suitable compounds are meta-phenylenediamine, para-phenylenediamine, 2,4-diaminotoluene, 2,6-diaminotoluene, 2-methyl-4,6-diethyl-1,3-phenylenediamine, 5-methyl-4,6-diethyl-1,3-phenylenediamine, 1,3-diamino-4-isopropylbenzene, and combinations thereof.

The halophthalic anhydrides employed according to the method of the present invention are typically cyclic anhydrides represented by structure V

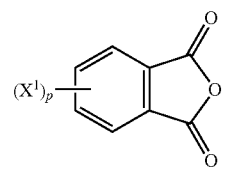

wherein $X^1$ is chloro, bromo, or fluoro, and p is an integer in a range from 1 to 4 inclusive. 4-chlorophthalic anhydride (CAS #118-45-6) is a preferred anhydride.

As noted, the method of the present invention employs a solvent. Thus, in step (A) of the method of the present invention a mixture comprising at least one halophthalic anhydride and at least one solvent is prepared. Preferably the solvent is an inert solvent. Suitable solvents include dichlorobenzenes, dimethylformamide, dimethylacetamide, N-methylpyrrolidone, dichlorotoluene, 1,2,4-trichlorobenzene, diphenyl sulfone, monoalkoxybenzenes such as anisole, and the like, and mixtures thereof. In a preferred embodiment, the inert solvent is chosen such that the boiling point of the solvent system is at least about 20° C. higher than the boiling point of water under the prevailing reaction conditions. The prevailing reaction conditions include the temperature and pressure at which the imidization reaction is carried out. In one embodiment, the imidization reaction is carried out under superatmospheric pressure (i.e. the pressure is greater than 1 atmosphere). Ortho-dichlorobenzene (o-DCB) is frequently a the solvent of choice for the reaction.

In one embodiment, the halophthalic anhydride is added to the solvent of choice with vigorous stirring while keeping the mixture hot. Temperatures greater than 150° C. are preferred. The solvent, the diamine and the halophthalic anhydride are typically combined in amounts such that the total solids content during the reaction to form the bis(halophthalimide) does not exceed about 25 percent by weight, more preferably the total solids content during the reaction to form the bis(halophthalimide) does not exceed about 17 percent by weight. "Total solids content" expresses the proportion of the reactants as a percentage of the total weight including liquids present in the reaction at any given time. In one embodiment, as solvent and water are distilled from the reaction mixture, additional solvent is added to maintain the total solids content within the preferred range. The terms total solids content and "% solids"

are used interchangeably herein. This is effected by the addition of solvent to compensate for any increase in solids content.

In a second step, step (B), at least one diamine is added to the mixture comprising the halophthalic anhydride and the solvent prepared in step (A) to form a reaction mixture. In one embodiment, the diamine compound is metered into the mixture formed in step (A). The diamine compound may be added either as a solid, a melt, or in solution in an inert solvent. In a preferred embodiment, the diamine compound is added as a hot melt at a an addition rate which is sufficiently slow to ensure sufficient mixing of the reactants and to avoid undue caking of solids in the reaction medium. The addition of the diamine compound is also carried out in such a fashion that the solids content of the reaction mixture is maintained at less than about 25% by weight, more preferably less than about 17% by weight. The reaction mixture formed in step (B) is said to be characterized by an "initial molar ratio of halophthalic anhydride to diamine". The "initial molar ratio of halophthalic anhydride to diamine" is the "actual" or "true" ratio of halophthalic anhydride moieties to diamine moieties present in the reaction mixture in step (B). As a result of the uncertainty in the weights of reactants used the "initial molar ratio of halophthalic anhydride to diamine" typically has a value which is different than the ratio calculated based upon the weights of halophthalic anhydride and diamine added in steps (A) and (B). Uncertainty in the weights of halophthalic anhydride and diamine used can be pronounced when large-scale reactions are being carried out. Moreover, a stoichiometric imbalance can lead to undesired consequences such as "clumping" of the product bis(halophthalimide). The "actual" molar ratio can be determined by performing a high performance liquid chromatography (HPLC) analysis on the reaction mixture after most of the reactants have been converted to the bis(halophthalimide) product.

With respect to the amounts of halophthalic anhydride and diamine employed, it is preferable to have an excess of the halophthalic anhydride in the reaction mixture. Preferably, 2.01 to 3.0 molar equivalents of the halophthalic anhydride with respect to the diamine compounds are employed, more preferably 2.01 to 2.5 molar equivalents of the halophthalic anhydride with respect to the diamine compound are employed.

Typically, the bis(halophthalimide) product is produced in a slurry form that is largely free from by-products and unreacted reactants, and isolation and purification of the bis(halophthalimide) product from the slurry is not required prior to polymerization to form polyetherimide.

In some embodiments an imidization catalyst may be added to the reaction mixture. Suitable imidization catalysts are known in the art. They include salts of organophosphorus acids, particularly phosphinates such as sodium phenylphosphinate (SPP) and heterocyclic amines such as 4-dimethylaminopyridine (DMAP). Organic and inorganic acids may also be used to catalyze this reaction. Suitable organic acids include chlorophthalic acid, phthalic acid, and acetic acid. Sodium phenylphosphinate is generally preferred. The catalyst, when opted for, may be added before the diamine compound has been added, after the diamine compound has been added, or together with the diamine compound. In a preferred embodiment of the present invention, the catalyst, when used in the reaction mixture, is added after the addition of the diamine compound.

Step (C) of the method of the present invention comprises heating the reaction mixture formed in step (B) to a temperature of at least 100° C., optionally in the presence of the imidization catalyst described. Typically the reaction mixture is heated to a temperature of at least 150° C., preferably in a range from about 150° C. to about 250° C., and more preferably in a range from about 175° C. to about 225° C. It should be noted that the reaction mixture may be heated at atmospheric pressure, subatmospheric pressure or superatmospheric pressure. When superatmospheric pressures are employed the pressure is typically up to about 5 atmospheres, to facilitate the conversion of starting materials to product bis(halophthalimide). Typically, step (C) also provides for the removal of at least some of the water of imidization resulting from reaction of the halophthalic anhydride with the diamine. In one embodiment, about 95% of the water of imidization is removed in step (C).

In step (D) the reaction mixture formed by the combination of steps (A)-(C) is analyzed to determine the "initial molar ratio of halophthalic anhydride to diamine". As noted, in conventional methods for the production of bis(halophthalimides), the amount of halophthalic anhydride present in the reaction mixture can only be roughly estimated based on the initial added amount. In one aspect of the invention, a suitable analytical tool may be employed to determine accurately the amount of each the reactants initially employed. This information may then be used to determine if any of the reactants need to be added to compensate for the deficiency of the same. In one embodiment of the invention, the analytical tool used to determine the initial molar ratio of halophthalic anhydride to diamine is a chromatographic method. In a typical embodiment of the present invention, a high performance liquid chromatography (HPLC) technique is used. Other analytical methods such as, but not limited to, gas chromatography, infra-red spectroscopy, ultraviolet spectroscopy, and the like may be used to monitor the reaction.

In step (E) any stoichiometric deficiency revealed by determining the initial molar ratio halophthalic anhydride to diamine (relative to the desired molar ratio) is corrected by the addition of halophthalic anhydride or diamine to achieve a "corrected molar ratio" of halophthalic anhydride to diamine. Typically, because the quantity of halophthalic anhydride or diamine needed to correct the stoichiometry is small, weighing errors can be minimized using small more reliable mass measuring equipment. The corrected molar ratio is generally much closer to the desired molar ratio of reactants than is the initial molar ratio. In a further embodiment of the invention, the analytical tool used to monitor the reaction mixture is also coupled to a controlling unit that is capable of automatically monitoring and correcting the stoichiometry between the reactants.

A further feature of the present invention is the solids content of the reaction mixture which at any given time during the course of the reaction should be typically less than 25% by weight, preferably in the range from about 10% to about 17% by weight. By "solids content" is meant the proportion of the reactants as a percentage of the total weight including liquids. This is effected by the addition of solvent to compensate for any increase in solids content.

Another embodiment of the present invention involves the removal of water from the reaction mixture. The water may be present in the system from a variety of sources; the reactor, or as a component of one or more of the reactants or solvents employed. Moreover, water is also produced as the by-product of the imidization reaction. Regardless of its origin, the presence of residual water in the product bis(halophthalimide) is detrimental to the polymerization reaction for which the bis(halophthalimide) is typically intended. Thus, in one aspect, the present invention provides a bis(halophthalimide) product which is suitable for use in a polymerization reaction to form polyetherimide. In one embodiment, at least 95% of the water present during step (C) of the reaction is removed from the reaction mixture during step (C) and the remaining water is removed during step (D). Water removal may be accomplished using means well-known in the art such as a distillation process. In one embodiment of the invention, the reactor is designed such that water is removed efficiently wherein the valves, nozzles, outlets, housings, and like features, of the reaction vessel are properly designed with low volume configuration (as for example, with flush mounted valves) and the reaction vessel is devoid of any water retention zones.

In one embodiment, the reaction vessel comprises spray nozzles from which hot solvent (e.g., hot o-DCB) is directed at the reactor walls and outlets in order to "chase" water from the reactor directing a spray of hot solvent on the interior surfaces of the reactor (typically surfaces which are above the level of the contents of the reaction vessel) serves to drive water adhering to the walls of the reactor from the reactor, and has the added benefit of washing solid reactants and product off of the reactor walls and back into the reaction mixture. In one embodiment, the solvent is o-DCB that is maintained at a temperature of at least about 180° C.

In another embodiment of the invention, the water removal is also effected by a "partial condensation" process. Partial condensation is a technique in which a multi-component vapor stream is subjected to a selective partial condensation by passage through a condenser maintained at a temperature greater than the boiling point of one or more of the lower boiling components but less than the boiling point of at least one higher boiling component. As the multi-component vapor stream encounters the condenser, the higher boiling components condense back to the liquid phase and may be returned to the source, whereas the components which boil at a temperature less than the temperature at which the condenser is maintained pass through the condenser, largely without condensing. It should be noted that this is extremely useful when trying to dry reaction mixtures comprising water and orthodichlorobenzene (o-DCB). Typically to dry such a reaction mixture by a simple distillation technique, roughly 10 volumes of o-DCB must be distilled per unit volume water distilled in order to dry the reaction mixture. The use of the partial condensation technique significantly lowers the amount of o-DCB which must be taken overhead with the water and thereafter separated from the water. It will be understood by those skilled in the art that the boiling points referred to are the boiling points of water and solvent under the conditions in the system. Water may be boiling at a temperature greater than or less than 100° C.

Those skilled in the art will understand that as a mixture of water and solvent are removed from the reaction vessel by distillation, at least a portion of the reactants and product may be entrained out of the reaction vessel with the water and solvent. Thus, in a further embodiment of this invention, the reactants and/or products and solvent that may have been entrained from the reaction vessel during the reaction are separated from a water phase and/or otherwise dried to remove water. The reactants and/or products and solvent are then recycled to the same reaction mixture or to a subsequent reaction mixture.

The bis(halophthalimide) produced from the reaction between the halophthalic anhydride and the diamine compound in an inert solvent may optionally be isolated through conventional techniques such as filtration, centrifugation and the like; or the slurry may be used as such for the next step viz. polymerization. It is within the scope of the present invention to use the slurry as such for making polymers.

In a further embodiment of the present invention, a phase transfer catalyst is added as a solution in the same inert solvent or in a different inert solvent or mixtures thereof, to the mixture comprising the product and an inert solvent and the resulting mixture is dried until it contains less than 20 ppm water. The phase transfer catalyst is used to effect polymerization. The drying is done under superatmospheric pressures at high temperatures, preferably at about 220° C. and 20 psig.

In one aspect of the invention, the bishalophthalimide is prepared using a stainless steel hot oil jacketed reaction vessel comprising the following features:

(A) a 4-blade turbine agitator
(B) reactor baffles
(C) re-pad nozzles on the top of the reactor to reduce space where water can get trapped
(D) zero volume agitator housing to reduce space where water can get trapped
(E) spray nozzles in the top of the tank that deliver a spray of hot (180° C.) o-DCB
(F) electro-polished sides to reduce the tendency of solids to adhere to the side of the vessel
(G) a zero-volume sample tap
(H) sufficient insulation to insure that the top of the vessel remains hot
(I) a second oil jacket that can be employed to heat the top of the reactor if necessary
(J) tempered oil loops that can control the temperature of the upper and lower jacket.

The agitator and the baffles were designed as described to ensure there is efficient mixing of the reaction mixture. This also ensures that there is sufficient contact between the reactants and that no local hot spots will be created. In one embodiment the baffles are approximately one inch in width and are separated from the reactor wall by a gap of about 7.6 cm (3 inches). In a further embodiment, the baffles have a height that does not exceed the operating liquid level in the tank.

In one embodiment the reactor is equipped with re-pad nozzles and zero volume agitator housing thereby further limiting undesired retention of water within the interior spaces of the reactor. In certain embodiments of the present invention the reactor is equipped with a "sample tap", which is used to draw samples out for analysis, said sample tap being "zero volume" to ensure no moisture can get trapped in the spaces e.g. piping) associated with the sample tap. The zero volume sample tap also provides that there is no wastage during the withdrawal of samples.

In one embodiment, the reactor comprises at least one hot-oil jacket. In certain embodiments, the top of the reactor is provided with a dedicated oil jacket to ensure greater control of the temperature. Typically, The reactor is provided with tempered oil loops that are capable of controlling the temperature of all sides of the reactor. Extra insulation is advantageously provided to ensure accurate control of the temperature. In one embodiment, the oil jacket is capable of maintaining the internal temperature of the reactor at least about 220° C. (425° F.).

In one embodiment, the internal surfaces of the reactor are made of stainless steel and are optionally electropolished. Electropolishing is a process that is used to smooth, polish, deburr and clean stainless steel by selectively removing irregular features on the metal surface. When electropolishing stainless steel, elemental iron is removed, and a layer of chromium-rich oxide forms on the surface. This oxide film is thickest over depressions and thinnest over projections. At the projections the electrical resistance is least and current density greatest; therefore, the effects of electropolishing are also the greatest in these locations. The oxide layer also provides for minimal moisture absorption, surface cleanliness and high corrosion resistance. Thus, in reactors which have been subjected to electropolishing the reactor walls are typically free of cracks and pits. In addition, solids typically do not adhere to the walls, thereby reducing caking of solids within the reactor.

Each of the reactor features discussed provide a greater measure of control over the reaction to form bis(halophthalimides). Thus, the reactor features disclosed help to ensure that (a) the reaction goes to completion; (b) by-products formation is minimized; (c) caking of solids or solids adhering to the walls of the reactor is minimized; and (d) the product bis(halophthalimide) comprises less than 20 ppm water.

It is also within the scope of the invention to produce polyetherimides from a mixture of solvent and bis(halophthalimide) produced according to the method of the present invention. In one embodiment, at least one comonomer as a slurry or a solution is added to the mixture of solvent and bis(halophthalimide). The at least one comonomer typically comprises a metal salt (e.g. the disodium salt of bisphenol A) of at least one bisphenol having structure VI

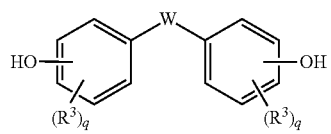

VI wherein $R^3$ is a halogen atom, a nitro group, a cyano group, a $C_1$-$C_{12}$ aliphatic radical, $C_3$-$C_{12}$ cycloaliphatic radical, or a $C_3$-$C_{12}$ aromatic radical; q is independently at each occurrence an integer from 0 to 4 inclusive; W is a bond, an oxygen atom, a sulfur atom or a selenium atom, an $SO_2$ group, an SO group, a CO group, a $C_1$-$C_{20}$ aliphatic radical, $C_3$-$C_{20}$ cycloaliphatic radical, or a $C_3$-$C_{20}$ aromatic radical. The reaction of the metal salt of biphenol VI with the bis(halophthalimide) prepared according to the method of the present invention affords polyetherimide compositions. Typically, the metal salt of the bisphenol is an alkali metal salt or an alkaline earth metal salt of the bisphenol. In an alternate embodiment, the at least one comonomer comprises a metal salt (e.g. the disodium salt of resorcinol) of a dihydroxy benzene. Dihydroxy benzenes are illustrated by resorcinol, hydroquinone, methylhydroquinone and the like.

Example 1

The following examples are set forth to provide those of ordinary skill in the art with a detailed description of how the methods claimed herein are evaluated, and are not intended to limit the scope of what the inventors regard as their invention. Unless indicated otherwise, parts are by weight, temperature is in ° C.

A 500-gallon stainless steel hot oil jacketed reactor with the configuration as described in the specifications was used for the reaction. The vessel was charged with chlorophthalic anhydride (ClPA)/o-dichlorobenzene (o-DCB) at about 12% solids content, 355.9 pounds of nominal dry weight ClPA. The material was heated to reflux before analysis by High Performance Liquid Chromatography (HPLC) to determine the molar ratio of diacids to anhydrides. The solution was also analyzed for 3- and 4-ClPA and phthalic anhydride. Phthalic anhydride was added at this stage as chain stopper.

Molten meta-phenylene diamine (mPD) (103.5 pounds nominal) was then slowly metered, over a 2 to 4 hour period to the reaction mixture that was maintained at a temperature in the range of about 175° C. to about 180° C. (350° F. to 356° F.), with agitation. The temperature of the oil on the jacket of the reactor was set at 204° C. (400° F.). The water of imidization and o-DCB was taken overhead and condensed. The % solids of ClPAMI in the reactor was not allowed to surpass 17% solids. Hot o-DCB was added to the reactor to keep the solids at the desired level (15 to 17%). The initial mPD charge was made intentionally 1.5 pounds deficient relative to the desired ratio of mPD to ClPA so that the ClPAMI product was anhydride rich. This was done to prevent sticking of the material to the sides of the vessel. At this level of solids content, the non-Newtonian mixture stirred with sufficient efficiency where the material was mixing well in the reactor and there were no stagnant areas in the tank.

Upon the completion of the mPD addition and after the bulk of the water had been removed from the tank, a sample of the reaction mixture was taken, and the stoichiometry of the reaction mixture was determined using HPLC. Additional ClPA solution was added until the stoichiometry of the ClPAMI was 0.05 to 0.3 mole % rich in ClPA with respect to the amount of mPD charged to the reactor. The analytical method worked very well when the bulk of the water had been removed. Running the reaction near reflux facilitated this. This resulted in a clean HPLC trace, and generally, there was no chlorophthalic acids present to complicate the determination of the stoichiometry. Additionally, most of the bis-amide-acids were ring closed, and most of the monoamine had reacted with ClPA. The ClPA and monoimides were clearly delineated in the HPLC trace resulting from running the reaction as described above.

Once the ClPAMI had been adjusted to the desired stoichiometry, Sodium Phenylphosphinate (SPP) imidization catalyst was added to the reaction mixture and the ClPAMI was dried in the level control mode at atmospheric pressure in the presence of the imidization catalyst. In this manner, o-DCB was removed from the tank while hot dry o-DCB was sprayed into the headspace of the reactor, while maintaining a constant level (weight) in the reactor. Any water lingering in the head of the reactor was thus forced up and out of the reactor. After the overheads of the reactor were dry (<20 ppm o-DCB), then enough o-DCB was removed from the tank to afford ClPAMI at 20 to 25% solids. This procedure resulted in insignificant amounts of ClPAMI adhered to the walls of the vessel. Any ClPAMI that did adhere to the wall was removed with a spray nozzle or was dissolved during the subsequent polymerization reaction (i.e., it was not strongly adhered to the walls). The slurry of ClPAMI was polymerized in ODCB in a manner analogous to that described in Example 3 below. This led to polymer with very low and acceptable levels of residual ClPAMI.

The general procedure as described in Example 1 was followed. In the final step, SPP imidization catalyst was left out of the reaction, and the ClPAMI was dried under pressure (18 to 25 psig), at a temperature in a range of from about 218° C. to about 250° C. (425° F. to 480° F.), at a solids contents of from about 15% to 17%. Hot o-DCB spray was used to chase water from the vessel in the level control mode. Once the overhead o-DCB was found to contain less than 20 ppm water, the pressure was relieved from the vessel and the amount of solid ClPAMI in the slurry was adjusted to a range of from about 20% to about 25% solids just prior to the polymerization reaction. The slurry of ClPAMI was polymerized in ODCB in a manner analogous to that described in Example 3 below.

Once the polymerization reaction was completed in the imidization/polymerization vessel, the reaction mixture was transferred to a quench vessel. The polymerization vessel was then washed with hot o-DCB to clean the imidization/polymerization vessel. This rinse was found to be free of ClPAMI and was then sent forward to the quench vessel and there was no residual ClPAMI adhered to the wall. The polymer made from this process contained less than 100 ppm ClPAMI. Polymer made from imidization batches where these conditions were not followed (e.g., higher solids content, higher oil temperature, or no stoic control during mPD addition) contained 1000 to 3000 ppm ClPAMI.

The o-DCB/water collected off the condenser of the reactor contained a precipitate thought to comprise ClPA and mPD adducts. o-DCB comprising this precipitate was subsequently used in the preparation of an additional batch of ClPAMI.

Example 3

A 500 gallon vessel mounted on weigh cells was charged with 350.5 pounds (nominal) of ClPA, 5% of which was 3-ClPA and 95% was 4ClPA, in 2340 pounds of ODCB. The ClPA contained 1.26 pounds of phthalic anhydride (PA). An additional 4.0 pounds of PA was then added. Sodium phenyl phosphate (SPP, 0.4 pounds) was then added. The mixture was heated to 175° C. with the use of a bottom hot oil jacket on the vessel. The hot oil temperature was 205° C. Molten mPD (104.9 pounds) was added to the vessel over a 2 hour period with agitation (The agitation was maintained throughout the imidization and polymerization steps). Water and ODCB was taken overhead, condensed and collected in an accumulator. The % solids of the reaction mixture was not allowed to exceed 17% (ODCB was added as necessary to ensure that the % solids was in the range of 15 to 17%. % Solids is defined by the weight of ClPAMI produced divided by the sum of the weights of ODCB present and the weight of ClPAMI produced. This formulation was to provide 575 pounds of polymer with a Mw of 45,000 grams per mole. The stoichiometry of the ClPAMI was analyzed by the HPLC method and it was found that 1.9 pounds of meta-phenylenediamine (mPD) had to be added to achieve the corrected molar ratio of halophthalic anhydride to diamine (target: ClPA rich by 0.015 mole %). The additional mPD was added at reflux and a sample was taken 30 minutes later, and the ClPAMI was found to be at the desired stoichiometry. The reaction mixture was not allowed to exceed 17% solids during this time. Hexaethyl guanidinium chloride (HEGCl) catalyst solution (15.3 pounds of 16.75% by weight HEGCl in ODCB containing less than 50 ppm water, corresponding to 2.6 pounds of dry catalyst and corresponding to 1.0 mole % catalyst with respect to moles BPA salt employed) was added to the ClPAMI slurry at 180° C. ODCB was stripped from the reaction mixture until the ClPAMI was at 18 to 20% solids. This solvent stripping step ensured that the ClPAMI slurry was dry. A 23.89% solids slurry of the disodium salt of bisphenol A ("BPA salt") had previously been prepared. This salt was slightly caustic rich (−0.05 mol % BPA deficient). 1065 pounds of salt slurry (maintained at 300° F.) was metered into the vessel containing the ClPAMI slurry over a 25 to 30 minute period. Heating of the reaction vessel was discontinued during the addition of the salt slurry. The reaction was exothermic and ODCB was allowed to distill overhead. Thereafter, the hot oil temperature on the vessel was then increased to 218° C. and ODCB was distilled off over a 4 hour period until the weight of the vessel indicated that the reaction mixture was at 30% solids (Here, % solids was defined by the weight of polymer produced divided by the sum of ODCB present and the amount of polymer produced). A sample of the polymerization reaction mixture was analyzed by GPC and it was found that additional BPA salt was needed to achieve the desired molecular weight. Thus, 41 pounds of salt slurry (the same material initially added to the vessel) was metered into the reaction vessel. Over the next two hours the vessel was maintained at 180 to 185° C. and sampled. Samples of the reaction mixture were analyzed by GPC, and it was determined that an additional 13 pounds of salt slurry was needed to hit the desired Mw. This amount of salt was added and the vessel sampled over the course of the next two hours. It was found by GPC that the desired Mw target was achieved (46,500). The material in the vessel was then transferred to a tank containing 1917 pounds of ODCB at 150° C. Phosphoric acid (6.75 pounds of 85% aqueous phosphoric acid) was added to the diluted reaction mixture at 165° C. In order to rinse the polymerization vessel 1917 pounds of hot ODCB was added to the polymerization vessel and the vessel was heated to reflux. This vessel rinse was then transferred to the dilution vessel to provide a polymer solution having a concentration of about 10% solids, containing the precipitated sodium chloride by-product. The Mw of the polymer was then determined to be 44,400 grams per mole. It was found that the polymer contained 195 ppm residual 4,4-ClPAMI and 223 ppm PAMI (with respect to the weight of polymer). The polymer solution was then processed in the conventional manner (Mott filter at 165° C. to remove the precipitated NaCl, followed by water washing at 95° C. using plate decanters). The resultant 10% polymer solution in ODCB solution contained less than 200 ppm HEG/PEG and no detectable NaCl. The polymer solution can then be subjected to extruder devolatilization in the conventional manner to provide polymer pellets.

The invention has been described in detail with particular reference to preferred embodiments thereof, but it will be understood by those skilled in the art that variations and modifications can be effected within the spirit and scope of the invention.

What is claimed is:

1. A method for preparing a bis(halophthalimide), said method comprising sequentially:
   (A) preparing a mixture comprising at least one halophthalic anhydride and at least one solvent wherein the mixture has a temperature greater than 150° C.,
   (B) adding to the mixture formed in step (A) at least one molten diamine to form a reaction mixture, said reaction mixture being characterized by "an initial molar ratio of halophthalic anhydride to diamine", wherein the at least one molten diamine has the formula $H_2N-A^1-NH_2$ wherein $A^1$ is a $C_2$-$C_{40}$ divalent aromatic radical;
   (C) heating the reaction mixture formed in step (B) to a temperature of at least 150° C., and removing water of imidization;
   (D) analyzing the reaction mixture formed by the combination of steps (A)-(C) to determine the initial molar ratio of halophthalic anhydride to diamine; and
   (E) adding anhydride or diamine to the mixture formed by the combination of steps (A)-(C) to achieve a "corrected molar ratio" of halophthalic anhydride to diamine, said initial molar ratio and corrected molar ratio being in a range between about 2.01 and about 2.3, and
   (F) adding sodium phenyl phosphinate imidization catalyst to the mixture and heating to a temperature of at least 100° C., to obtain a bis(halophthalimide) product mixture that is substantially free of water.

2. The method according to claim 1 wherein said analyzing the reaction mixture formed by the combination of steps (A)-(C) to determine the initial molar ratio of halophthalic anhydride to diamine, comprises determining a concentration of halophthalic anhydride, a concentration of by-product halophthalic acid, and a concentration of intermediate monophthalimide monoamine in the reaction mixture formed by the combination of steps (A)-(C).

3. The method according to claim 1 wherein said bis(halophthalimide) has structure I

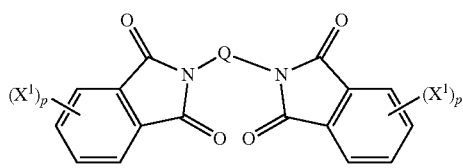

wherein $X^1$ and $X^2$ are independently fluorine, chlorine, bromine or iodine; and Q is a $C_2$-$C_{20}$ divalent aliphatic radical, a $C_2$-$C_{40}$ divalent aromatic radical, or a $C_4$-$C_{20}$ divalent cycloaliphatic radical; p is independently at each occurrence an integer ranging from 1 to 4.

4. The method according to claim 1 wherein the halophthalic anhydride is 4-chlorophthalic anhydride, 3-chlorophthalic anhydride, 4-fluorophthalic anhydride, 3-fluorophthalic anhydride, or a mixture comprising at least two of the foregoing.

5. The method according to claim 1 wherein the solvent is selected from the group consisting of chlorobenzene, o-dichlorobenzene, anisole, toluene, xylene, and mesitylene.

6. The method according to claim 1 wherein the solvent is o-dichlorobenzene.

7. The method according to claim 1 wherein the at least one diamine is selected from the group consisting of oxydianiline, and bis(4-aminophenyl)sulfone.

8. The method according to claim 1 wherein said diamine is selected from the group consisting of aromatic diamines III and diamines IV

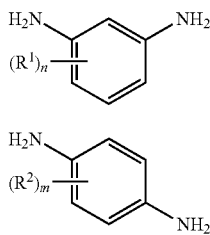

wherein $R^1$ and $R^2$ are independently at each occurrence a halogen atom, a nitro group, a cyano group, a $C_2$-$C_{20}$ aliphatic radical, a $C_2$-$C_{40}$ aromatic radical, or a $C_4$-$C_{20}$ cycloaliphatic radical; and "n" and "m" are independently integers ranging from 0 to 4.

9. The method according to claim 8 wherein the aromatic diamine is selected from the group consisting of meta-phenylene diamine and para-phenylene diamine.

10. The method according to claim 1 wherein the temperature of the reaction mixture in step (C) is at least 200° C.

11. The method according to claim 1 wherein the halophthalic anhydride, and the diamine when taken together are present in an amount corresponding to an initial solids content of the reaction mixture in a range from about 5% to about 25% by weight.

12. The method according to claim 1 wherein said analyzing comprises analysis by liquid chromatography, gas chromatography, or a combination thereof.

13. The method according to claim 1 wherein at least one of steps (A)-(C) and (E) is performed in a reactor free of water retention zones.

14. The method according to claim 1 wherein at least one of steps (A)-(C) and (E) is performed in a reactor equipped with at least one flush-mounted valve.

15. The method according to claim 1 wherein step (E) comprises distilling a mixture of water and organic components, to produce a product mixture that is substantially free of water and a distillate comprising water, solvent, unreacted halophthalic anhydride, and diamine.

16. The method according to claim 15 wherein said distillate is subjected to water removal and recycling.

17. The method according to claim 16 wherein said recycling comprises at least one process step selected from the group consisting of (a) preparing a mixture comprising at least one halophthalic anhydride and at least one solvent, (b) adding at least one diamine to the mixture comprising at least one halophthalic anhydride and at least one solvent, to form a reaction mixture, wherein a portion of the at least one of said halophthalic anhydride, said solvent, and said diamine is provided by said distillate.

18. The method according to claim 15 wherein said distilling is carried out at superatmospheric pressure.

19. The method according to claim 1 wherein each of steps (A)-(C) and (E) is characterized by a percent solids content, said percent solids content being less than about 17% solids.

20. The method according to claim 1 wherein in step (B), said diamine is added dropwise.

21. The method according to claim 1 wherein step (C) and step (E) comprise distilling water from the reaction mixture through a condenser maintained at a temperature greater than the boiling point of water and less than the boiling point of the solvent, wherein the boiling point of the solvent is greater than the boiling point of water.

22. The method according to claim 21 wherein said distilling is carried out at a pressure of at least 1 atmosphere.

23. The method according to claim 21 wherein a difference between the boiling point of water and solvent is at least 20° C.

24. A method for preparing a bis(chlorophthalimide); said method comprising sequentially:
(A) preparing a mixture comprising 3-chlorophthalic anhydride, 4-chlorophthalic anhydride and at least one solvent having a temperature greater than 150° C.;
(B) adding to the mixture formed in step (A) at least one molten aromatic diamine, to form a reaction mixture, said reaction mixture being characterized by an initial molar ratio of 3-chlorophthalic anhydride and 4-chlorophthalic anhydride to aromatic diamine, wherein the at least one molten diamine has the formula $H_2N$-$A^1$-$NH_2$ wherein $A^1$ is a $C_2$-$C_{40}$ divalent aromatic radical;
(C) heating the reaction mixture formed in step (B) optionally in the presence of an imidization catalyst, to a temperature of at least 150° C., and removing water of imidization;
(D) analyzing the reaction mixture formed by the combination of steps (A)-(C) to determine the initial molar ratio of 3-chlorophthalic anhydride and 4-chlorophthalic anhydride to aromatic diamine; and (E) adding a mixture of 3-chlorophthalic anhydride and 4-chlorophthalic anhydride, or aromatic diamine to the reaction mixture formed by the combination of steps (A)-(C) to achieve a corrected molar ratio of 3-chlorophthalic anhydride and 4-chlorophthalic anhydride to aromatic diamine, said initial molar ratio and corrected molar ratio being in a range between about 2.01 and about 2.3, and (F) adding sodium phenyl phosphinate imidization catalyst to the mixture and heating to a temperature of at least 100° C., to obtain a bis(chlorophthalimide) product mixture that is substantially free of water.

25. A method for preparing a bis(4-chlorophthalimide); said method comprising sequentially:

(A) preparing a mixture comprising 4-chlorophthalic anhydride and orthodichlorobenzene having a temperature greater than 150° C.;

(B) adding to the mixture formed in step (A) a molten mixture of meta-phenylene diamine and para-phenylene diamine, to form a reaction mixture, said reaction mixture being characterized by an initial molar ratio of 4-chlorophthalic anhydride to meta-phenylene diamine and para-phenylene diamine, said adding being carried out and removing water of imidization;

(C) heating the reaction mixture formed in step (B), to a temperature of at least 150° C.;

(D) analyzing the reaction mixture formed by the combination of steps (A)-(C) to determine the initial molar ratio of 4-chlorophthalic anhydride to meta-phenylene diamine and para-phenylene diamine; and (E) adding 4-chlorophthalic anhydride, or a mixture of meta-phenylene diamine and para-phenylene diamine to the reaction mixture formed by the combination of steps (A)-(C) to achieve a corrected molar ratio of 4-chlorophthalic anhydride to meta-phenylene diamine and para-phenylene diamine, said initial molar ratio and corrected molar ratio being in a range between about 2.01 and about 2.3, and (F) adding sodium phenyl phosphinate imidization catalyst and heating to a temperature of at least 100° C. to obtain a bis(4-chlorophthalimide) product mixture that is substantially free of water.

26. The method according to claim 1, wherein $A^1$ is a $C_6$-$C_{40}$ divalent aromatic radical.

27. The method according to claim 1, wherein the at least one molten diamine is selected from the group consisting of 1,4-diaminonaphthalene, 2,6-diaminonapthalene, 4,4'diaminobiphenyl, oxydianiline, bis(4-aminophenyl)sulfone, meta-phenylene diamine, para-phenylene diamine, 2,4-diaminotoluene, 2,6-diaminotoluene 2-methyl-4,6-diethyl-1,3-phenylenediamine, 5-methyl-4,6-diethyl-1,3-phenylene diamine, 1,3-diamino-4-isopropylbenzene, and combinations thereof.

28. The method according to claim 24, wherein $A_1$ is a $C_6$-$C_{40}$ divalent aromatic radical.

29. The method according to claim 24, wherein the at least one molten diamine is selected from the group consisting of 1,4-diaminonaphthalene, 2,6-diaminonapthalene, 4,4'diaminobiphenyl, oxydianiline, bis(4-aminophenyl)sulfone, meta-phenylene diamine, para-phenylene diamine, 2,4-diaminotoluene, 2,6-diaminotoluene 2-methyl-4,6-diethyl-1,3-phenylenediamine, 5-methyl-4,6-diethyl-1,3-phenylene diamine, 1,3-diamino-4-isopropylbenzene, and combinations thereof.

30. The method according to claim 1, wherein the initial molar ratio is from 2.01 to about 2.3.

31. The method according to claim 1, wherein the initial molar ratio is from about 2.03 to about 2.3.

* * * * *